United States Patent
Solberg

(10) Patent No.: US 10,617,331 B1
(45) Date of Patent: Apr. 14, 2020

(54) SYSTEMS AND METHODS FOR DETECTING IF A TREADMILL USER IS RUNNING OR WALKING

(71) Applicant: Brunswick Corporation, Mettawa, IL (US)

(72) Inventor: James R. Solberg, Palatine, IL (US)

(73) Assignee: Life Fitness, LLC, Lake Forest, IL (US)

( * ) Notice: Subject to any disclaimer, the term of this patent is extended or adjusted under 35 U.S.C. 154(b) by 73 days.

(21) Appl. No.: 15/950,581

(22) Filed: Apr. 11, 2018

(51) Int. Cl.
*A61B 5/11* (2006.01)
*A61B 5/00* (2006.01)
(Continued)

(52) U.S. Cl.
CPC .......... *A61B 5/1123* (2013.01); *A61B 5/4866* (2013.01); *A61B 5/7253* (2013.01);
(Continued)

(58) Field of Classification Search
CPC ...... A63B 22/02–0292; A47B 2220/06; A01K 15/027; G06F 2203/012; B62M 1/34;
(Continued)

(56) References Cited

U.S. PATENT DOCUMENTS 5,382,207 A    1/1995  Skowronski et al.
5,474,087 A *  12/1995 Nashner ............... A61B 5/1036
                                                     482/54
(Continued)

FOREIGN PATENT DOCUMENTS

CA    2758710 A1 *  5/2013  ............... A61B 5/11
CN    101087633 B     9/2012
(Continued)

OTHER PUBLICATIONS

Sejdic et al, A comprehensive assessment of gait accelerometry signals in time, frequency and time-frequency domains, IEEE Trans Neural Syst Rehabil Eng. May 2014 ; 22(3): 603-612. doi:10.1109/TNSRE.2013.2265887. (Year: 2014).*
(Continued)

*Primary Examiner* — Randy W Gibson
*Assistant Examiner* — David L Singer
(74) *Attorney, Agent, or Firm* — Andrus Intellectual Property Law, LLP

(57) ABSTRACT

A method for detecting whether a user is walking or running. The method includes detecting foot interactions of the user and outputting data from the foot interactions detected. The method includes calculating a cadence frequency based on the data from the foot interactions, and measuring a first signal amplitude detected at a first multiplier of the cadence frequency calculated and a second signal amplitude for the data from the foot interactions detected at a second multiplier of the cadence frequency using the data from the foot interactions. The method includes comparing the first signal amplitude and the second signal amplitude to determine a cadence factor, then comparing the cadence factor to a predetermined threshold. The method detects whether the user is walking or running is based upon the comparison of the cadence factor to the predetermined threshold.

20 Claims, 8 Drawing Sheets

(51) Int. Cl.
*A63B 24/00* (2006.01)
*A63B 22/02* (2006.01)

(52) U.S. Cl.
CPC ............ *A61B 5/742* (2013.01); *A63B 22/025* (2015.10); *A63B 24/0062* (2013.01); *A63B 24/0075* (2013.01); *A63B 2024/0093* (2013.01); *A63B 2220/53* (2013.01); *A63B 2220/833* (2013.01); *Y10S 482/901* (2013.01)

(58) Field of Classification Search
CPC .......... G06K 9/00348; B66B 21/10–12; A61B 5/112; A61B 5/1123; A61B 5/1038
USPC ...................... 482/54; 119/700; 198/324–325
See application file for complete search history.

(56) References Cited

U.S. PATENT DOCUMENTS

| | | | |
|---|---|---|---|
| 5,583,776 A * | 12/1996 | Levi ..................... | A43B 3/0005 701/400 |
| 5,747,955 A | 5/1998 | Rotunda et al. | |
| 5,856,736 A | 1/1999 | Rotunda et al. | |
| 6,095,984 A * | 8/2000 | Amano et al. ..... | A61B 5/02438 600/481 |
| 6,491,647 B1 | 12/2002 | Bridger et al. | |
| 6,783,482 B2 | 8/2004 | Oglesby et al. | |
| 7,507,187 B2 | 3/2009 | Dyer et al. | |
| 7,914,420 B2 | 3/2011 | Daly et al. | |
| 8,157,708 B2 | 4/2012 | Daly et al. | |
| 8,403,814 B2 | 3/2013 | Daly et al. | |
| 8,551,026 B2 | 10/2013 | Alwan et al. | |
| 8,574,131 B2 | 11/2013 | Daly et al. | |
| 9,052,798 B1 | 6/2015 | Klassen et al. | |
| 9,072,930 B2 | 7/2015 | Ashby et al. | |
| 9,470,705 B2 | 10/2016 | Statham | |
| 9,494,446 B2 | 11/2016 | Murray et al. | |
| 9,517,378 B2 | 12/2016 | Ashby et al. | |
| 9,618,527 B2 | 4/2017 | McGown | |
| 9,622,686 B1 | 4/2017 | Berme et al. | |
| 10,018,481 B1 * | 7/2018 | Shekhar ............... | G01C 22/006 |
| 10,360,510 B1 * | 7/2019 | Al-Amin ................ | G06N 7/005 |
| 2005/0209061 A1 * | 9/2005 | Crawford ........... | A63B 22/0056 482/54 |
| 2006/0160667 A1 | 7/2006 | Oglesby et al. | |
| 2008/0214360 A1 * | 9/2008 | Stirling ................ | A61B 5/1038 482/9 |
| 2008/0275348 A1 * | 11/2008 | Catt ....................... | A61B 5/1112 600/483 |
| 2009/0023556 A1 * | 1/2009 | Daly ................... | A63B 22/0235 482/9 |
| 2010/0160115 A1 | 6/2010 | Morris et al. | |
| 2011/0190097 A1 * | 8/2011 | Daly ................... | A63B 22/0235 482/9 |
| 2012/0165159 A1 * | 6/2012 | Daly ................... | A63B 22/0235 482/9 |
| 2013/0054181 A1 * | 2/2013 | Lakhzouri .............. | G01C 21/16 702/141 |
| 2013/0085711 A1 * | 4/2013 | Modi .................... | G01C 22/006 702/141 |
| 2013/0165297 A1 * | 6/2013 | Daly ................... | A63B 22/0235 482/9 |
| 2015/0066422 A1 * | 3/2015 | Zhang ................. | G01C 22/006 702/141 |
| 2016/0007885 A1 | 4/2016 | Basta et al. | |

FOREIGN PATENT DOCUMENTS

| | | | | |
|---|---|---|---|---|
| DE | 4027317 C1 * | 12/1991 | .......... | A61B 5/1038 |
| DE | 102004058563 A1 | 6/2006 | | |
| EP | 3090685 A1 * | 11/2016 | .......... | A61B 5/1118 |

OTHER PUBLICATIONS

Sejdic et al, Extraction of Stride Events From Gait Acceleronnetry During Treadmill Walking, IEEE Journal of Translational Engineering in Health and Medicine vol. 4, 2016 (Year: 2016).*
Hamill et al, Shock attenuation and stride frequency during running, Human Movement Science 14 (1995) 45-60 (Year: 1995).*
Mathworks, Human Activity Classification based on Smartphone Sensor Signals (Year: 2015).*
Grankin et al, Research of MEMS accelerometer features in mobile phone, Conference Paper Nov. 2012 (Year: 2012).*

\* cited by examiner

SYSTEMS AND METHODS FOR DETECTING IF A TREADMILL USER IS RUNNING OR WALKING

FIELD

The present disclosure generally relates to detecting whether a treadmill user is running or walking, and more particularly to automatically and accurately detecting whether a treadmill user is running or walking based on detected foot interactions.

BACKGROUND

The Background and Summary are provided to introduce a foundation and selection of concepts that are further described below in the Detailed Description. The Background and Summary are not intended to identify key or essential features of the claimed subject matter, nor are they intended to be used as an aid in limiting the scope of the claimed subject matter.

The following U.S. Patents and Patent Applications are incorporated herein by reference:

U.S. Pat. No. 5,382,207 discloses an exercise treadmill configured to improve tracking, the treadmill being provided with a frame including molded plastic pulleys, having an integral gear belt sprocket, an endless belt extending around the pulleys, and a motor operatively connected to the rear pulley to drive the belt. The pulleys are molded out of plastic and have a diameter of approximately nine inches. A mold and method for producing large diameter treadmill pulleys having an integrally molded sprocket are also disclosed. A deck underneath the running surface of the belt is supported by resilient members. A positive lateral belt tracking mechanism is used to correct the lateral position of the belt. A belt position sensor mechanism is used in combination with a front pulley pivoting mechanism to maintain the belt in the desired lateral position on the pulleys. The exercise treadmill also includes a lift mechanism with an internally threaded sleeve engaged to vertically aligned nonrotating screws. A user display of foot impact force on the belt is also provided.

U.S. Pat. No. 6,783,482 discloses a microprocessor based exercise treadmill control system that includes various features to enhance user operation. These features include programs operative to: permit a set of user controls to cause the treadmill to initially operate at predetermined speeds; permit the user to design custom workouts; permit the user to switch between workout programs while the treadmill is in operation; and perform an automatic cooldown program where the duration of the cooldown is a function of the duration of the workout or the user's heart rate. The features also include a stop program responsive to a detector for automatically stopping the treadmill when a user is no longer on the treadmill and a frame tag module attached to the treadmill frame having a non-volatile memory for storing treadmill configuration, and operational and maintenance data. Another included feature is the ability to display the amount of time a user spends in a heart rate zone.

U.S. Pat. No. 7,914,420 discloses sensing applications for exercise machines. An example sensing application for profiling a workout session of an exercise machine comprises selecting at least one workout parameter or inputting at least one physical characteristic of a user and operating the exercise machine in compliance with the at least one workout parameter selected. The method further comprising reading output signal values from a sensor in which the output signals are generated by a user impact to the exercise machine during the exercise session and processing the output signals. The method further comprising determining workout matrices to profile the exercise session using the processed output signals and providing feedback information based on the workout matrices.

U.S. Pat. No. 8,157,708 discloses sensing applications for exercise machines. An example sensing application for profiling a workout session of an exercise machine comprises a user interface to input physical characteristics or workout parameters. A sensor is operatively coupled to the exercise machine to generate an output signal in proportion to a magnitude of a force imparted on the exercise machine in response to an impact to the exercise machine. A control system processes the output signal to determine a magnitude of a peak or trough value of the output signal, where the control system is to process the peak or trough value of the output signal to profile the exercise session.

U.S. Pat. No. 8,403,814 discloses methods for profiling exercise sessions. An example method for profiling an exercise session includes receiving physical characteristics or workout parameters via an input interface, generating output signals proportional to a magnitude of vertical forces imparted to the exercise machine by a user during the exercise session, and processing the output signals via a control system to determine the magnitude of peak or trough values of the output signals to profile the exercise session.

U.S. Pat. No. 8,574,131 discloses methods for profiling exercise sessions. An example method of determining cadence of a user disclosed herein includes receiving output signals from a sensor generated in response to consecutive footfalls of the user impacting a deck of a treadmill during an exercise session and processing the output signals from the sensor to determine respective magnitude values of a peak or a trough value of each of the output signals. The method includes detecting whether a first output signal has a first peak or trough value and detecting whether a second output signal has a second peak or trough value, determining a time interval between the first peak or trough value detected and the second peak or trough value detected, and calculating a cadence value of the user based on the time intervals.

U.S. Patent Application Publication No. 2006/0160667 discloses a microprocessor based exercise treadmill control system that includes various features to enhance user operation. These features include programs operative to: permit a set of user controls to cause the treadmill to initially operate at predetermined speeds; permit the user to design custom workouts; permit the user to switch between workout programs while the treadmill is in operation; and perform an automatic cooldown program where the duration of the cooldown is a function of the duration of the workout or the user's heart rate. The features also include a stop program responsive to a detector for automatically stopping the treadmill when a user is no longer on the treadmill and a frame tag module attached to the treadmill frame having a non-volatile memory for storing treadmill configuration, and operational and maintenance data. Another included feature is the ability to display the amount of time a user spends in a heart rate zone.

SUMMARY

One embodiment of the present disclosure generally relates to a method for detecting whether a user is walking or running on a surface. The method includes the steps of detecting foot interactions between a foot of the user and the surface and outputting data from the foot interactions detected. The method further includes calculating with a processing module a cadence frequency for the user based on the data from the foot interactions, measuring with the processing module a first signal amplitude for the data from the foot interactions detected at a first multiplier of the cadence frequency calculated for the user, and measuring with the processing module a second signal amplitude for the data from the foot interactions detected at a second multiplier of the cadence frequency calculated for the user. The method further includes comparing with the processing module the first signal amplitude and the second signal amplitude to determine a cadence factor, and comparing the cadence factor to a predetermined threshold. The method further includes detecting whether the user is walking or running based upon the comparison of the cadence factor to the predetermined threshold.

Another embodiment of the present disclosure generally relates to a non-transitory computer readable medium storing a program for detecting whether a user is walking or running on a surface that when executed by a processing module is configured to perform steps. The steps include receiving data from foot interactions detected by a sensor, calculating a cadence frequency for the user based on the data from the foot interactions, measuring a first signal amplitude for the data from the foot interactions detected at a first multiplier of the cadence frequency calculated for the user, and measuring a second signal amplitude for the data from the foot interactions detected at a second multiplier of the cadence frequency calculated for the user. The steps further include comparing the first signal amplitude and the second signal amplitude to determine a cadence factor, and comparing the cadence factor to a predetermined threshold. The steps further include detecting whether the user is walking or running based upon the comparison of the cadence factor to the predetermined threshold.

Another embodiment of the present disclosure generally relates to a system for detecting whether a user is walking or running on a surface. The system includes a foot interaction sensor configured to detect foot interactions between a foot of the user and the surface, and also configured to output data from the foot interactions detected. A processing module in communication with the foot interaction sensor is configured to receive the data from the foot interaction sensor. A memory module in communication with the processing module stores a program that is executable by the processing module. The processing module by executing the program is configured to calculate a cadence frequency from the data received from the foot interaction sensor, to measure a first signal amplitude for the data detected at a first multiplier of the cadence frequency calculated, and to measure a second signal amplitude for the data detected at a second multiplier at twice the cadence frequency calculated. The processing module is further configured to compare the first signal amplitude and the second signal amplitude to determine a cadence factor. The program also stores a predetermined threshold and the processing module is configured to compare the cadence factor to the predetermined threshold. The processing module determines whether the user is walking or running based upon the comparison of the cadence factor to the predetermined threshold.

BRIEF DESCRIPTION OF THE DRAWINGS

The drawings illustrate the best mode presently contemplated of carrying out the disclosure. The same numbers are used throughout the drawings to reference like features and like components. In the drawings.

DETAILED DISCLOSURE

Figure 1:
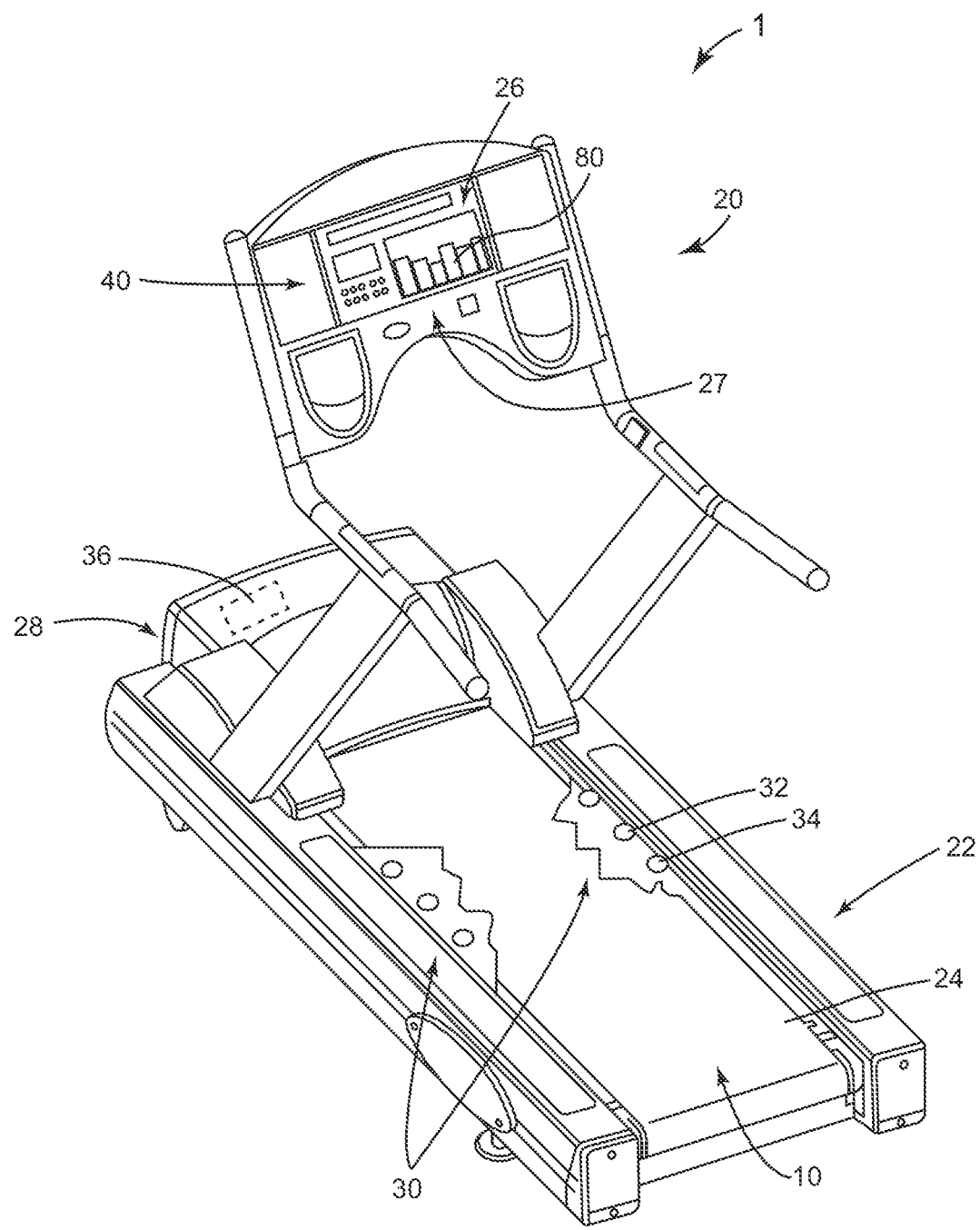
FIG. 1 is an isometric view of a treadmill incorporating systems for performing processes according to the present disclosure.

This written description uses examples to disclose embodiments of the present application, including the best mode, and also to enable any person skilled in the art to practice or make and use the same. The patentable scope of the invention is defined by the claims and may include other examples that occur to those skilled in the art. Such other examples are intended to be within the scope of the claims if they have structural elements that do not differ from the literal language of the claims, or if they include equivalent structural elements with insubstantial differences from the literal language of the claims.

In the present description, certain terms have been used for brevity, clarity, and understanding. No unnecessary limitations are to be implied therefrom beyond the requirement of the prior art because such terms are used for descriptive purposes only and are intended to be broadly construed. The different systems and methods described herein may be used alone or in combination with other systems and methods. Various equivalents, alternatives, and modifications are possible within the scope of the appended claims. Each limitation in the appended claims is intended to invoke interpretation under 35 USC § 112(f), only if the terms "means for" or "step for" are explicitly recited in the respective limitation.

There are two distinct types of human gait: walking, and running. Walking is defined as a gait cycle in which there is always at least one foot in contact with the ground (or another surface) at any given point in time. In contrast, running is defined as a gait cycle having an airborne phase, whereby there are instances in which neither foot is in contact with the ground. Within the context of fitness and training, it is often important to identify whether the exerciser is walking or running. First, this information is useful to know and log the duration in which the person has walked versus run, which may help the person identify trends overtime and track performance relative to personal goals. Additionally, the distinction between walking and running has a profound impact on the number of calories burned by the person in doing so. In this regard, the determination of whether a person is walking or running is an important input into the determination of a calorie expenditure for the person at that time. In the case of a person running on a treadmill, for example, this information is often shown on the treadmill display, on paired wearable devices, and/or is tracked elsewhere for long term performance monitoring.

Systems and methods known in the art presently rely upon the speed of the user for determining whether that user is walking or running. For example, if a user is travelling at a rate of 1 mph, it is a generally safe presumption that the user is presently walking. Likewise, if the user is travelling at a rate of 8 mph, it is almost certain that the user must be running (presuming a typical user of average height and physiology). However, the present inventor has identified that the particular demarcation for separating walking from running based on user speed is imprecise, both across and within users. This creates a high potential for improper assignment when it comes to calorie expenditure calculations and the like, particularly at speeds in which running and walking are each feasible. For example, systems and methods known in the art may assign a speed threshold of 4.5 mph. In this example, a tread speed of at least 4.5 mph would be automatically determined by the treadmill to correspond to the user running, whereas a treadmill tread speed of less than 4.5 mph would lead to a determination that the user is walking. However, the present inventor has identified it is very possible for a user to either power walk at a speed exceeding a normal threshold such as 4.5 mph, or to run at a slower rate below the threshold. In these cases, the user's gait would be inaccurately assigned by the systems and methods known in the art.

While tread speed is certainly a helpful factor in determining whether a user is running or walking (i.e., that 5 mph is likely running), the present inventor has identified that improved accuracy is needed. Through experimentation and development, the present inventor has identified the presently disclosed systems and methods for more accurately determining the user's gait based on detected data from the foot interactions of the user on a surface, such as a treadmill.

FIG. 1 depicts an exemplary treadmill 20 configured for detecting whether a user is running or walking according to the present disclosure. The treadmill 20 of the system 1 has a deck 22 with a belt 24 that is driven by a drive system 28 in the customary manner. A display 26 and a user interface 27 are used for controlling and programming the treadmill 20, as well as for displaying data collected by the system 1, including a calorie expenditure 80 for the user, which is discussed below.

The system 1 further includes one or more foot interaction detectors 30, which detect interactions between the user's foot and the belt 24 or deck 22 when the treadmill 20 is in use. The belt 24, deck 22, or any other surface in which the user may run is also collectively referred to as the surface 10. In an exemplary embodiment of the present system 1, the foot interaction detectors 30 include an accelerometer 32 and a displacement sensor 34, which detects the vertical displacement of the deck 22 as the user runs on the surface 10 of the belt 24. Additional foot interaction is also detectable using additional sensors, such as a motor current sensor 36, and through monitoring of the belt 24 speed with a belt speed sensor and/or motor commands for the drive system 28 (not shown) as descried in U.S. Pat. No. 8,574,131 and known in the art. It should be recognized that while only one foot interaction detector 30 is necessary, the combination of detected data from multiple sensors provides redundancy and increased accuracy for detecting whether the user is running or walking by providing additional data points for analysis.

Figure 2:
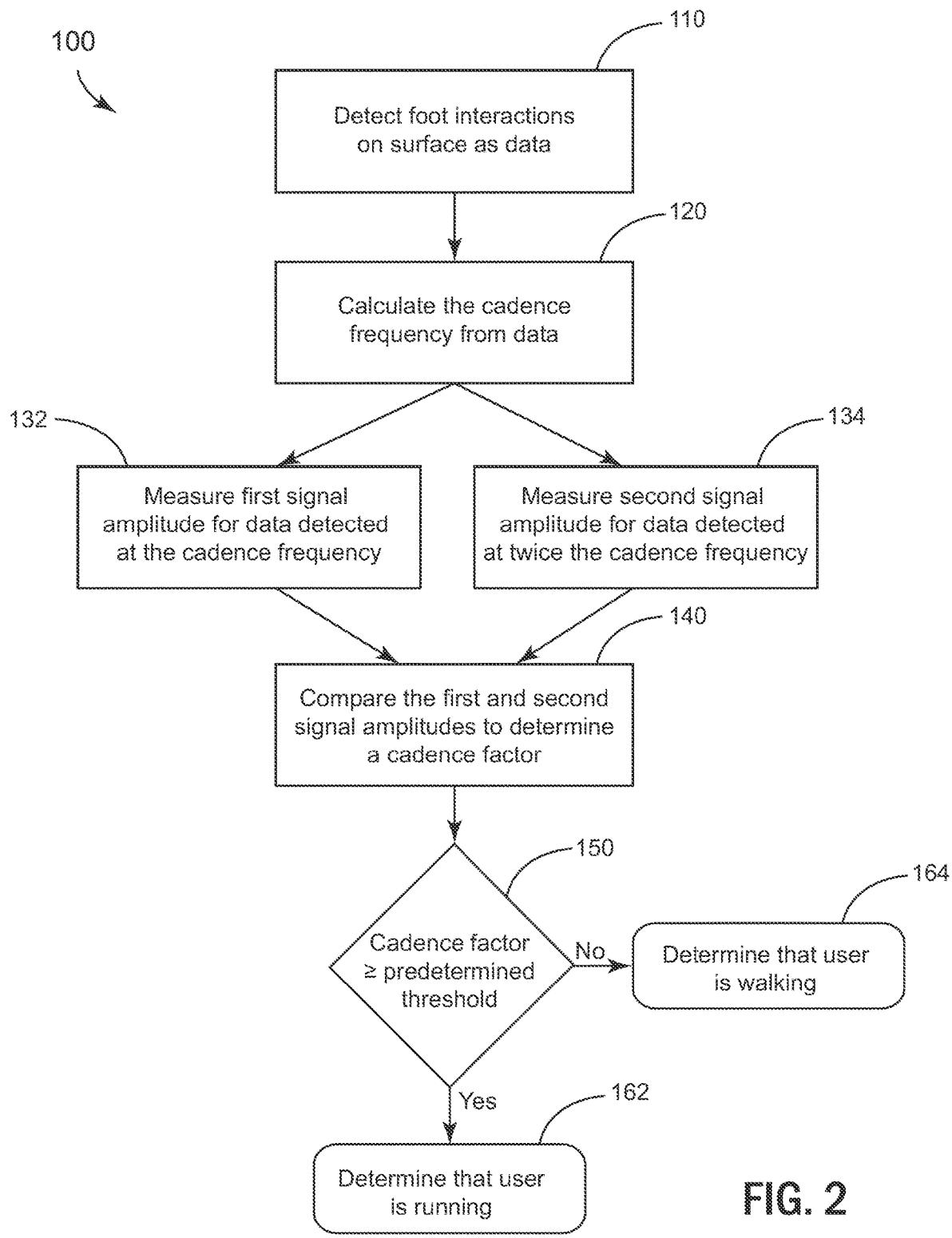
FIGS. 2 and 3 depict exemplary processes according to the present disclosure.
Figure 3:
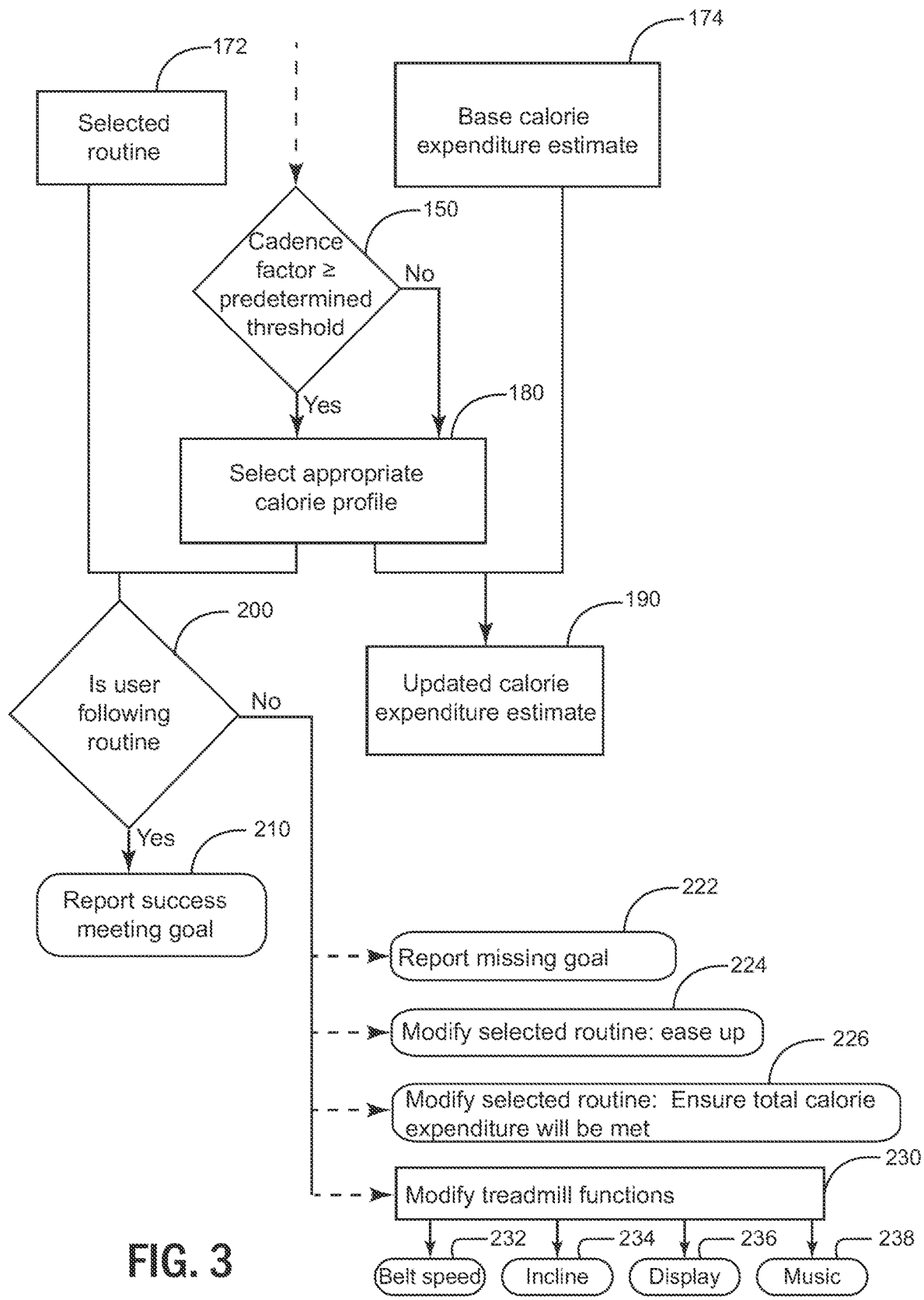

FIGS. 2 and 3 depict exemplary methods 100 by which the system 1 determines whether the user is running or walking, such as on the treadmill 20 of FIG. 1. To begin, the method 100 of FIG. 2 includes detecting foot interactions on a surface, such as the belt 24 previously discussed, as data from the treadmill 20 in step 110. Using this foot interactions data, the cadence or cadence frequency of the user's gait is calculated as a frequency in step 120, such as through the methods discussed in U.S. Pat. No. 8,574,131. For example, if the gait cycle repeats at a rate of once every second, the cadence frequency will be calculated to be 1 Hz.

It should be recognized that any transform methods known in the art may be used for estimating the power spectral density of the one or more sensors detecting foot interactions of the user and subsequently determining the cadence thereof. Common methods known in the art for detecting cadence include Fourier analysis and peak finding. In certain embodiments, the present inventor identified that Welch's method was particularly suited for use with the methods presently disclosed herein. As previously stated, different numbers and types of sensors may be used, which while all capable of detecting foot interactions, may require different predetermined thresholds and/or techniques for comparison.

Figure 5:
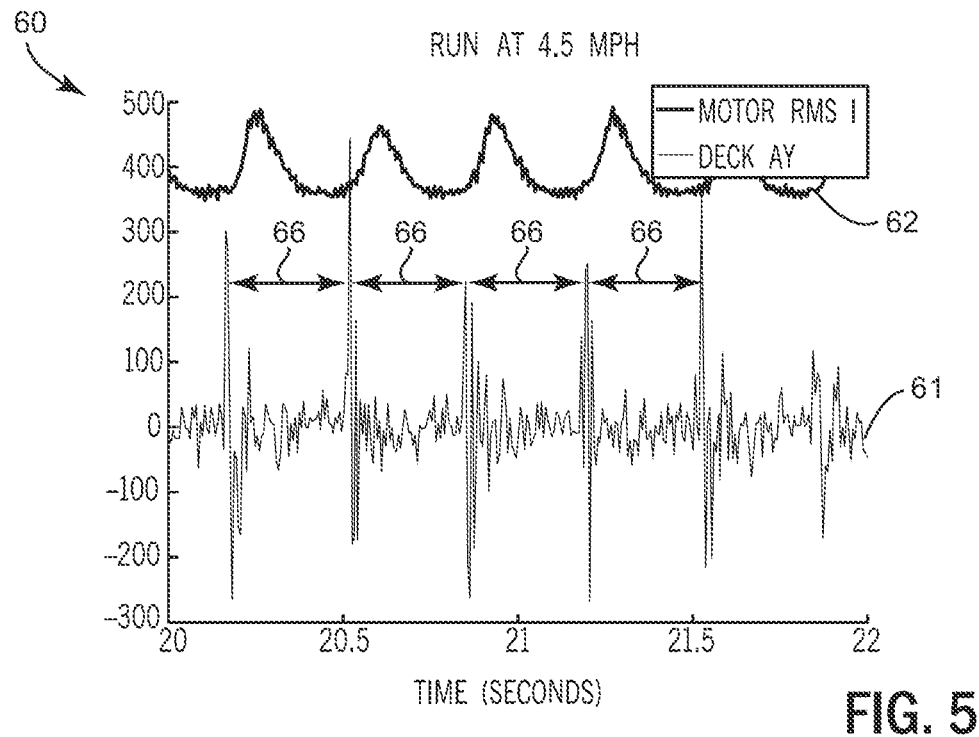
FIGS. 5-12 depict exemplary data collected and generated using the processes of FIGS. 2 and 3 according to the present disclosure.
Figure 6:
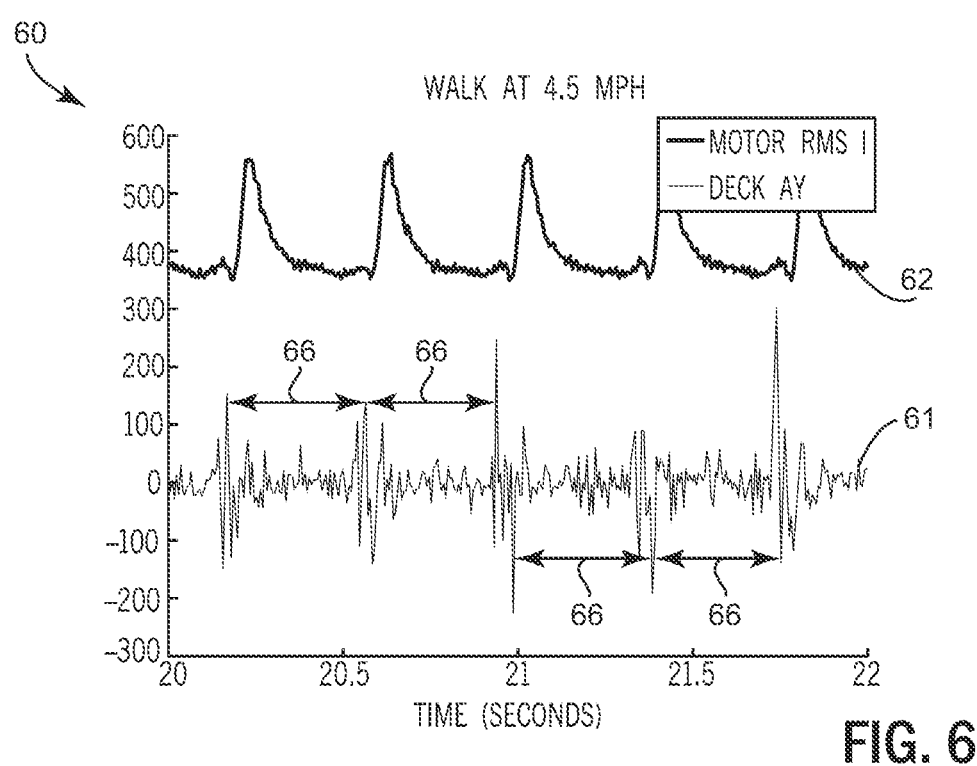

FIGS. 5 and 6 depict exemplary data collected from a user both running and walking at 4.5 mph, respectively. The data was collected from the motor current sensor 36 within the drive system 28 previously described, which was used to generate a motor current waveform 62. Concurrently, an accelerometer 32 and/or a displacement sensor 34 coupled to the deck 22 was used to detect movement to generate the deck movement waveform 61. As can be seen, the gait cycle is shown to repeat every 0.3-0.4 seconds, with the cadence frequency 66 between each cycle identified.

Figure 7:
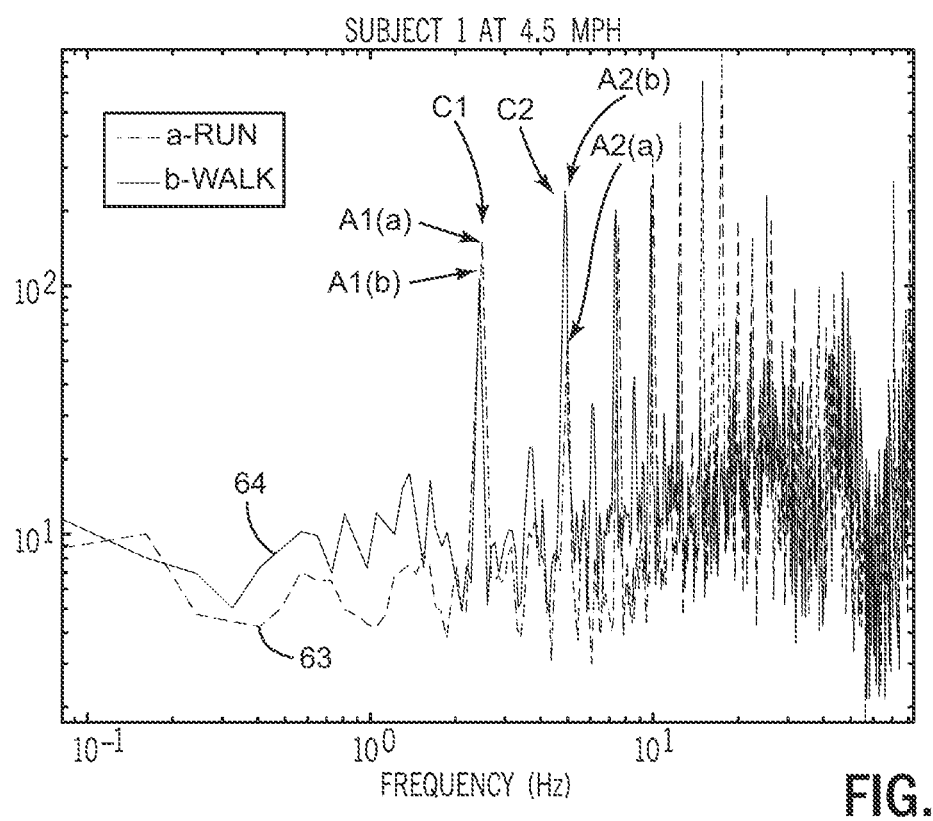
Figure 8:
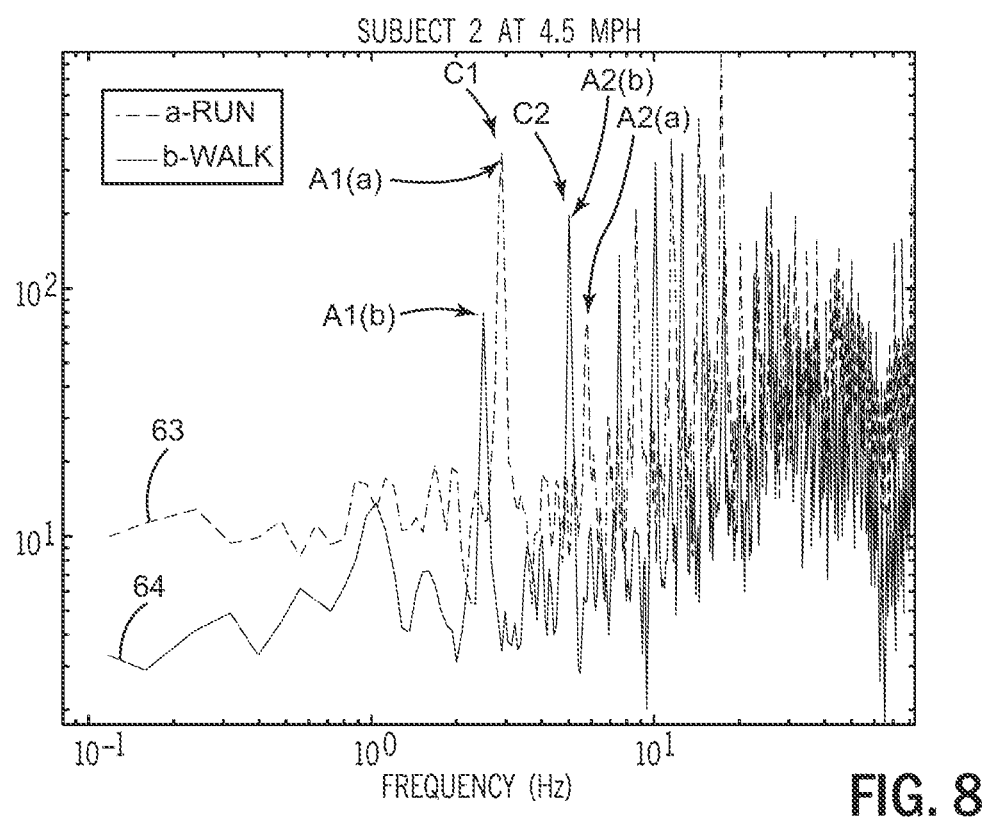
Figure 9:
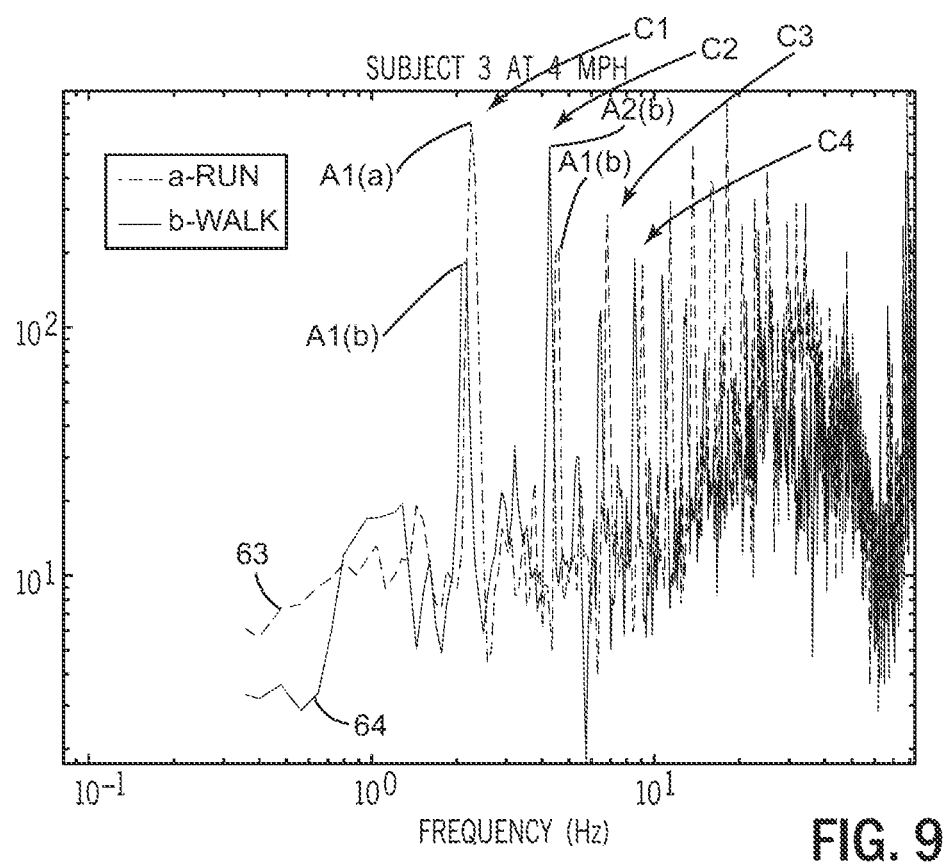

FIGS. 7-9 show similar data collected from three subjects, all both running and walking at the same speed, plotted in the frequency domain. The dashed lines (a-RUN) correspond to each user running and the solid lines (b-WALK) correspond to the same user walking at the same speed. Through experimentation and development, the present inventor has identified that the power of the data collected from foot interactions with the surface generate peaks at multiples of the cadence frequency 66 (shown as C1-C4 corresponding to the first multiplier C1 through the fourth multiplier C4) when using the systems 1 and methods 100 described herein. The amplitudes of the data at these peaks are calculated and shown as a first signal amplitude A1 (A1($a$) for running and A1($b$) for walking) for data collected at a frequency corresponding to the first multiplier C1 of the cadence frequency 66, and as second signal amplitudes A2 for data corresponding to the second multiplier C2 (or two times the cadence frequency 66).

Returning to FIG. 2, the method 100 includes these steps of measuring the first signal amplitude A1 from the data detected in step 110 at the cadence frequency 66, as well as measuring the second signal amplitude A2 for data collected from step 110 at twice the cadence frequency 66 in steps 132 and 134, respectively. In other words, steps 132 and 134 measure in the power of the signal data collected at the cadence frequency 66, and at two times the cadence frequency 66, as previously described with respect to FIGS. 7-9. Next, the first signal amplitude A1 and the second signal amplitude A2 are compared in step 140 to determine a cadence factor 70. In one exemplary embodiment, the cadence factor 70 is determined by taking the ratio of the first signal amplitude A1 and the second signal amplitude A2. However, other methods for comparing these measurements are also anticipated by the present disclosure.

The method 100 then includes comparing the cadence factor at 70 determined in step 140 to a predetermined threshold 54 in step 150. If in step 150 it is determined that the cadence factor 70 is greater than or equal to the predetermined threshold 54, it will be determined that the user is running in step 162. In contrast, if it is determined in step 150 that the cadence factor 70 is less than the predetermined threshold 54, it will be determined that the user is walking in step 164. It should be recognized that as with the present disclosure anticipating other methods for comparing the first signal amplitude A1 and the second signal amplitude A2 to determine the cadence factor 70, a variety of predetermined thresholds 54 may also be provided for comparison in step 150. Such predetermined thresholds 54 may be based on empirical data and the particular comparison involved, including details about a particular user, such as height.

Through experimentation and development, the present inventor has identified that in certain embodiments the cadence factor 70 as determined herein is greater when a user is running than when that same user is walking, including at the same speed (such as 4.5 mph). The present inventor has developed the present systems 1 and methods 100 to detect differences in the distinctive pattern of the user's foot interacting with the surface 10 of the treadmill 20 based on gait type. In certain instances, running (whereby foot interactions follow an airborne phase) results in foot interactions on the surface 10 that approximate a bouncing-off motion somewhat like a ricochet. In this case, all of the data collected for the foot interaction in step 110 occurs in a substantially short segment of time, which also corresponds to the cadence frequency 66. In contrast, the present inventor has identified that when the user is walking, distinctive foot interactions are detectable on the surface 10 of the treadmill 20 for both the landing of a particular foot, and the subsequent takeoff of that same foot. Accordingly, data collected from the foot interactions of a user who is walking occurs not only at a brief instance in the gait cycle, but at two distinct times for each foot within the gait cycle. Accordingly, the power or amplitude of the data collected from the foot interactions from a user who is walking does not occur only at the cadence frequency 66, but more frequently as well. In other words, the data from foot interactions when running is effectively concentrated at the cadence frequency 66, whereas the same user when walking has data spread across additional frequencies as well. In this manner, taking a ratio of the first signal amplitude A1 (corresponding to the one times the cadence frequency 66 at the first multiplier C1) and the second signal amplitude A2 (two times the cadence frequency 66 at the second multiplier C2) results in a greater number when the user is running, since the numerator is greater when the user is running.

Figure 10:
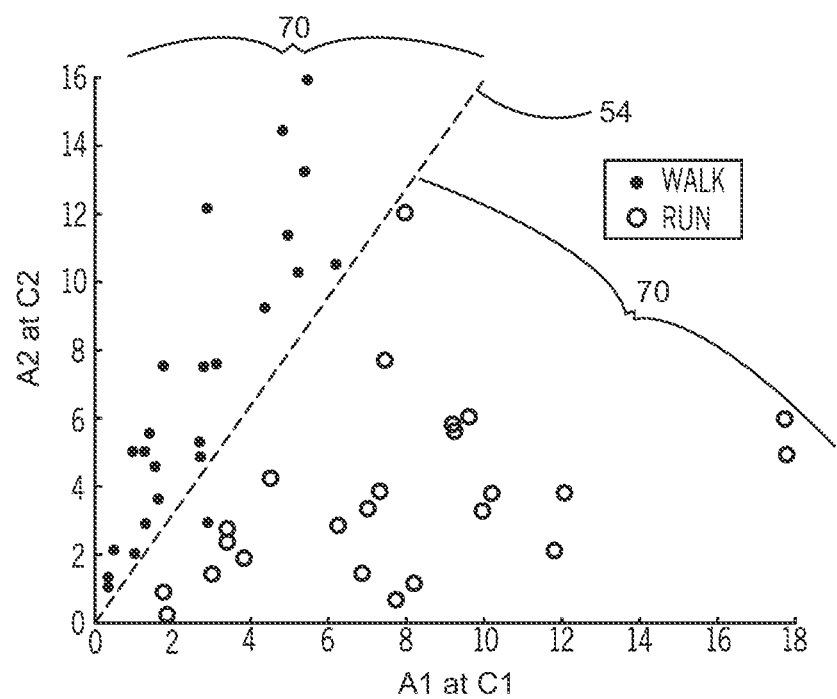
Figure 11:
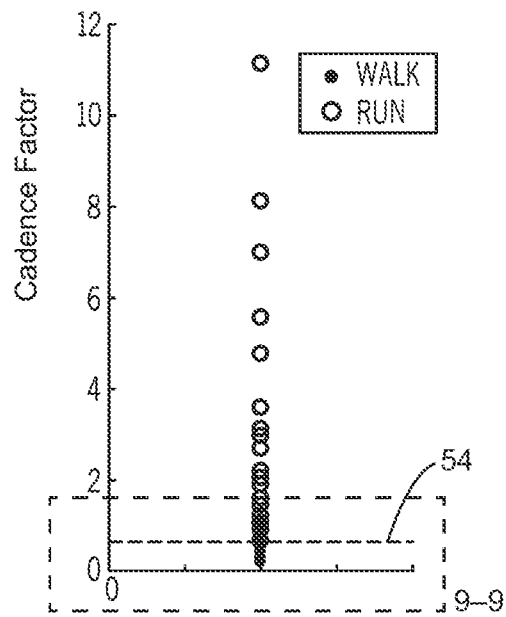
Figure 12:
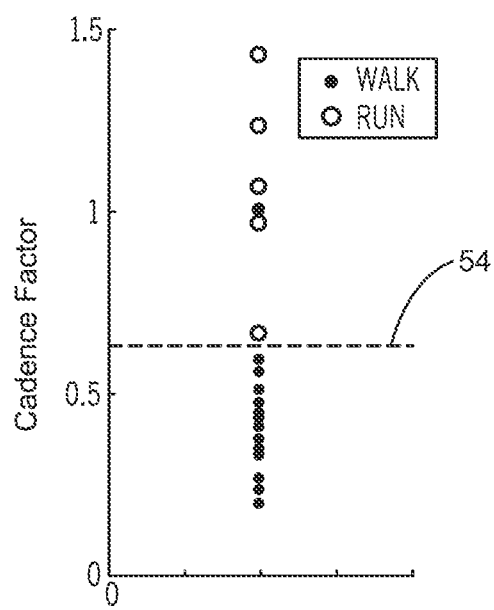

Empirical data collected for users walking and running at 4.5 mph, and the corresponding first signal amplitude A1 and second signal amplitude A2, can be seen in FIG. 10. A clear delineation can be seen between walking and running based on the data collected and generated according to the presently disclosed methods 100. In accordance with step 140, cadence factors 70 were also calculated, specifically as a ratio of the first signal amplitude A1 and the second signal amplitude A2 for each given user, which is shown in FIG. 11. A close-up is shown in FIG. 12. As can be seen in the present embodiment, a line at approximately 0.66 delineates the data collected for users running (shown in open circles) from data of the user's walking (shown in closed circles). Based on this empirical data, a predetermined threshold 54 of 0.66 would be an appropriate selection for this exemplary system 1 and method 100.

It should be recognized that while the previous example calculated the cadence factor 70 for comparison to the predetermined threshold 54 as a ratio of the first signal amplitude A1 to the second signal amplitude A2 (collected at a first multiplier C1 and a second multiplier C2 of the cadence frequency 66, respectively), other multipliers may also be used for this determination. For example, it can be seen in the data of FIG. 9 that foot interaction data at odd multipliers of the cadence frequency 66 (shown here as C1 and C3) is generally higher when a user is running than walking, whereas the opposite is true when examining even multipliers of the cadence frequency 66 (C2 and C4). In this regard, further embodiments of the present disclosure determine the cadence factor 70 by comparison of multipliers of the cadence frequency 66 other than the first multiplier C1 and the second multiplier C2, such as a comparison between the second multiplier C2 and the third multiplier C3. Certain embodiments further incorporate comparison across more than two multipliers, for both accuracy and redundancy of data.

Now continuing from the method 100 previously shown at FIG. 2, FIG. 3 depicts additional steps that in some embodiments are carried out after step 150 previously discussed. In certain embodiments, once it is determined in step 150 whether the cadence factor 70 is greater than, equal to, or less than the predetermined threshold 54, an appropriate calorie profile 52 would be selected in step 180. As will be discussed later, a plurality of calorie profiles 52 is stored within the system 1, at least including a calorie profile 52 corresponding to a user running, and another corresponding to the same user walking. This calorie profile 52 is selected in step 180 based on the determination of whether the user is walking or running from the comparison of the cadence factor 70 to the predetermined threshold 54 in step 150. This selection of the appropriate calorie profile 52 in step 180 is in certain embodiments applied to a base calorie expenditure estimate in step 174. In certain embodiments, the base calorie expenditure estimate is an estimation of the calories consumed by the user during operation of the treadmill 20, which may include the tread speed of the belt 24, the height and weight of the user, the incline of the treadmill 20, and other factors known in the art. By applying the appropriate calorie profile 52 selected in step 180 to the base calorie expenditure estimate from step 174, an updated calorie expenditure estimate can be provided in 190. This results in an accurate and automatic estimation of the user's caloric expenditure that is not reliant solely on tread speed, as with devices presently known in the art.

The method depicted in FIG. 3 further incorporates comparing the appropriate calorie profile 52 selected in step 180 with a selected routine (step 172) that the user has chosen in the user interface 27 of the treadmill 20. For example, the selected routine of step 172 may be a training program in which the user is directed to be running for a certain duration, but at a speed in which it is possible that the user may in fact be walking at the dictated speed. In the regard, step 200 is to determine whether the user is following the selected routine 172, based upon the selected calorie profile 52 from step 180. In other words, step 200 includes detecting whether the user's actual gait (running or walking) matches the prescribed selected routine from step 172.

In the embodiment shown, if the user is determined to be following the routine in step 200, step 210 includes reporting success of meeting this goal, which may include some kind of visual indicator on the display 26 of the treadmill 20, or elsewhere for tracking purposes, such as on a wearable device 12, or in cloud-based tracking modules 14. In contrast, if the user is determined to not be presently following the routine in step 200, a number of actions may be taken by the system 1. In certain embodiments, the system 1 will report missing the goal in step 222, which may occur on the display 26 or elsewhere, as previously discussed with respect to reporting success of meeting the goal in step 210. The system 1 may alternatively or additionally modify the selected routine from step 172, in some cases easing up to encourage the user to get back on track in step 224. As an alternative or addition, the selected routine from step 172 may be modified in step 226 to ensure that the total caloric expenditure associated with the selected routine will be met. For example, if the user is walking instead of running and thereby consuming fewer calories, the workout routine may be extended such that the user walks for a longer duration to meet the overall intended calorie expenditure.

The system 1 may also or alternatively use the determination that the user is not following the routine in step 200 to modify various treadmill functions in step 230. By way of example, this may include modifying the belt speed in step 232, or modifying the incline of the treadmill 20 in step 234 in the manners known in the art. Likewise, the display 26 may be updated to reflect either missing the goal in step 236, or with words of encouragement or other motivations to get the user back on track. Similarly, the treadmill 20 may queue up or change music being played by the treadmill 20 or a paired wearable device 12 in step 238, such as playing a song that the user has designated to be particularly motivating.

Figure 4:
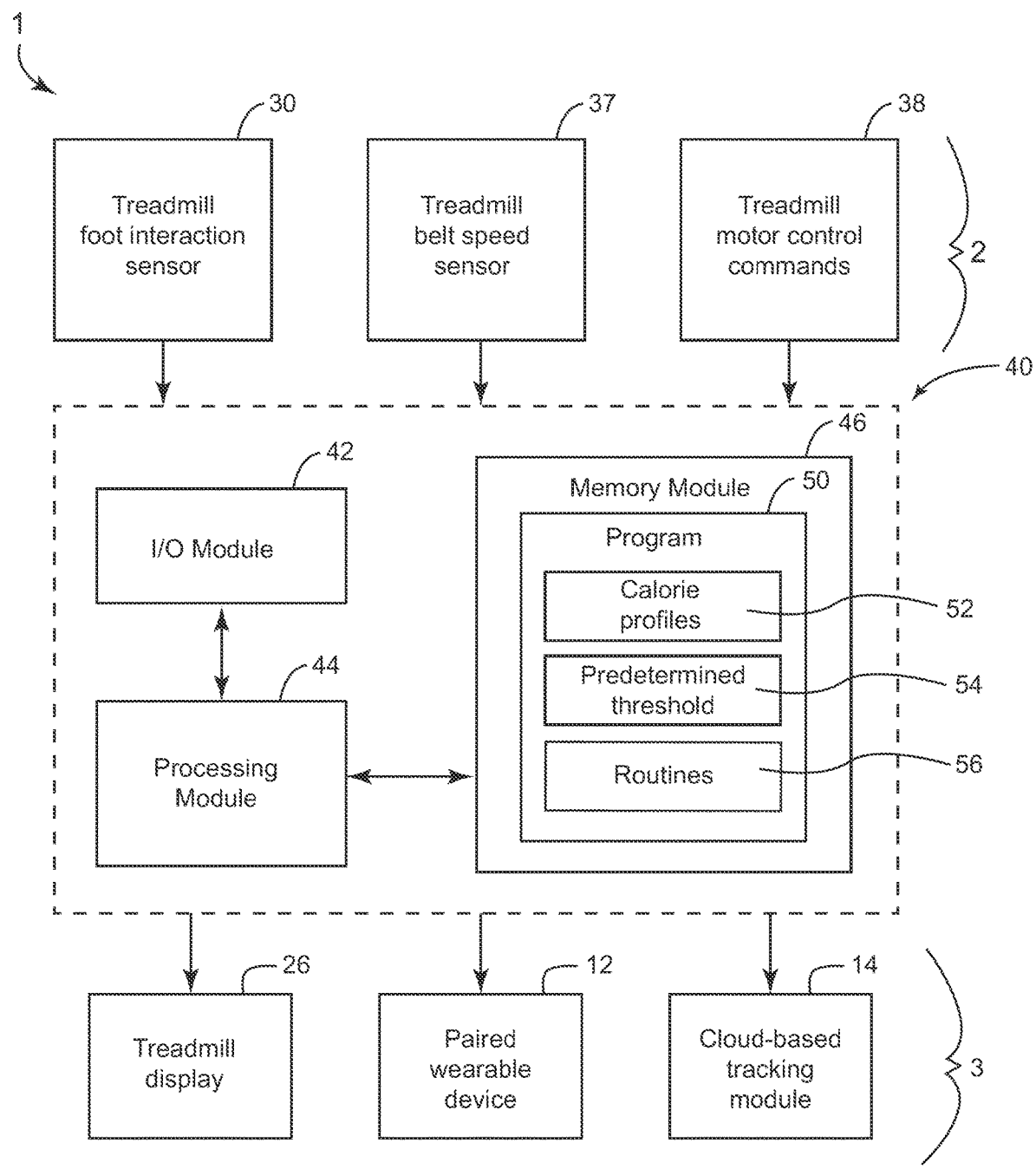
FIG. 4 is a schematic view of an exemplary system configured to execute the processes shown in FIGS. 2 and 3.

FIG. 4 depicts an exemplary system 1 configured to perform the methods 100 depicted in FIGS. 2 and 3. In the exemplary embodiment shown, signals and other information are received as inputs 2 within the electronics 40 from a variety of sources. Exemplary inputs 2 include one or more treadmill foot interaction sensors 30, a treadmill belt speed sensor 37, and/or a treadmill motor control command 38. As previously discussed, the treadmill foot interaction sensor 30 may include an accelerometer 32, a displacement sensor 34, and/or another device capable of detecting foot interactions between the user and the belt 24 of the treadmill 20. The belt speed sensor 37, motor control command 38, and other inputs 2 may be those presently known in the art and employed on treadmills 20 in the customary manner.

The electronics 40 in the present embodiment includes an I/O module 42 for communicating between the inputs 2 previously discussed, and a processing module 44. The processing module 44 is configured to execute instructions of a program 50 stored within a memory module 46, which is also in communication with the processing module 44. Exemplary programs 50 include instructions for executing the methods 100 previously discussed, as well as containing the calorie profiles 52, predetermined threshold 54, and the routines 56 previously discussed. It should be recognized that the program 50 may contain additional stored elements, or may divide those previously discussed into different groupings or structures. Likewise, it should be recognized that the schematic depiction of FIG. 4 merely exemplifies one configuration for communication within and between the elements of the electronics 40 and to the inputs 2 and outputs 3 generally.

It should be recognized that the programs 50 may be stored on a non-transitory tangible computer readable medium. The programs 50 may also include stored data. Non-limiting examples of the non-transitory tangible computer readable medium are nonvolatile memory, magnetic storage, and optical storage. As used herein, the term module may refer to, be part of, or include an application-specific integrated circuit (ASIC), an electronic circuit, a combinational logic circuit, a field programmable gate array (FPGA), a processor (shared, dedicated, or group) that executes code, or other suitable components that provide the described functionality, or a combination of some or all of the above, such as in a system-on-chip. The term module may include memory module 46 (shared, dedicated, or group) that stores code executed by the processing module 44. The terms program 50 or code, as used herein, may include software, firmware, and/or microcode, and may refer to programs, routines, functions, classes, and/or objects. The term shared, as used above, means that some or all code from multiple modules may be executed using a single (shared) processing module 44. In addition, some or all code to be executed by multiple different processing modules 44, and may be stored by a single (shared) memory module 46. The term group, as used above, means that some or all code comprising part of a single module may be executed using a group of processing modules. Likewise, some or all code comprising a single module modules 46 may be stored using a group of memory modules 46.

In the embodiment shown, the outputs 3 from the electronics 40 include communication with the treadmill display 26, a paired wearable device 12, such as a Bluetooth® smartwatch or other pairable device, and/or cloud-based tracking modules 14. For example, the cloud-based tracking module 14 may be an online performance and monitoring app that tracks progress of the user over time. It may also include communication and consultation with a trainer for remote personal training and performance coaching.

What is claimed is:

1. A method for detecting whether a user is walking or running on a surface, the method including the steps of:
   detecting foot interactions between a foot of the user and the surface and outputting data from the foot interactions detected;
   calculating with a processing module a cadence frequency for the user based on the data from the foot interactions;
   measuring with the processing module a first signal amplitude for the data from the foot interactions detected at a first multiplier of the cadence frequency calculated for the user;
   measuring with the processing module a second signal amplitude for the data from the foot interactions detected at a second multiplier of the cadence frequency calculated for the user;
   comparing with the processing module the first signal amplitude and the second signal amplitude to determine a cadence factor, and comparing the cadence factor to a predetermined threshold; and
   detecting whether the user is walking or running based upon the comparison of the cadence factor to the predetermined threshold.

2. The method according to claim 1, wherein a calorie expenditure for the user is calculated and displayed based on the data from the foot interactions, and wherein the calorie expenditure is based on one of a plurality of calorie profiles, further comprising selecting the one of the plurality of calorie profiles for the calorie expenditure based on the determination of whether the user is walking or running.

3. The method according to claim 2, wherein the surface is a belt of a treadmill, and wherein the calorie expenditure is displayed on the treadmill.

4. The method according to claim 3, wherein the one of the plurality of calorie profiles is combined with other factors to calculate the calorie expenditure.

5. The method according to claim 3, wherein the treadmill is configured to perform a plurality of functions, further comprising modifying how the treadmill performs at least one of the plurality of functions based on the determination of whether the user is walking or running.

6. The method according to claim 5, wherein the at least one of the plurality of functions includes comparing the data from the foot interactions to a preselected training routine.

7. The method according to claim 1, wherein an accelerometer is used to detect the foot interactions.

8. The method according to claim 7, wherein the surface is a belt of a treadmill, and wherein the accelerometer is coupled to a deck that supports the belt.

9. The method according to claim 1, wherein the first multiplier is the cadence frequency, wherein the second multiplier is twice the cadence frequency, and wherein the first signal amplitude is divided by the second signal amplitude to determine the cadence factor.

10. The method according to claim 9, wherein the user is determined to be running when the cadence factor is greater than the predetermined threshold, and wherein the predetermined threshold is 1.0.

11. A non-transitory computer readable medium storing a program for detecting whether a user is walking or running on a surface that when executed by a processing module is configured to perform the steps of:
    receiving data from foot interactions detected by a sensor;
    calculating a cadence frequency for the user based on the data from the foot interactions;
    measuring a first signal amplitude for the data from the foot interactions detected at a first multiplier of the cadence frequency calculated for the user;
    measuring a second signal amplitude for the data from the foot interactions detected at a second multiplier of the cadence frequency calculated for the user;
    comparing the first signal amplitude and the second signal amplitude to determine a cadence factor, and comparing the cadence factor to a predetermined threshold; and
    detecting whether the user is walking or running based upon the comparison of the cadence factor to the predetermined threshold.

12. The non-transitory computer readable medium according to claim 11, further comprising calculating a calorie expenditure for the user based on the data from the foot interactions, wherein the calorie expenditure is based on one of a plurality of calorie profiles stored in the program, further comprising selecting the one of the plurality of calorie profiles for the calorie expenditure based on the determination of whether the user is walking or running.

13. The non-transitory computer readable medium according to claim 12, wherein the surface is a belt of a treadmill, and further comprising displaying the calorie expenditure calculated on the treadmill.

14. The non-transitory computer readable medium according to claim 13, wherein the one of the plurality of calorie profiles is combined with other factors to calculate the calorie expenditure.

15. The non-transitory computer readable medium according to claim 13, wherein the program is further configured for the treadmill to perform a plurality of functions, further comprising modifying how the treadmill performs at least one of the plurality of functions based on the determination of whether the user is walking or running.

16. The non-transitory computer readable medium according to claim 15, wherein the at least one of the plurality of functions includes comparing the data from the foot interactions to a preselected training routine.

17. The non-transitory computer readable medium according to claim 11, wherein the sensor is an accelerometer, and wherein the accelerometer is coupled to a deck that supports the belt.

18. The non-transitory computer readable medium according to claim 11, wherein the first multiplier is the cadence frequency, wherein the second multiplier is twice the cadence frequency, and wherein the first signal amplitude is divided by the second signal amplitude to determine the cadence factor.

19. The non-transitory computer readable medium according to claim 18, wherein the user is determined to be running when the cadence factor is greater than the predetermined threshold, and wherein the predetermined threshold is 1.0.

20. A system for detecting whether a user is walking or running on a surface, the system comprising:
    a foot interaction sensor configured to detect foot interactions between a foot of the user and the surface, and configured to output data from the foot interactions detected;
    a processing module in communication with the foot interaction sensor, wherein the processing module is configured to receive the data from the foot interaction sensor;
    a memory module in communication with the processing module, wherein the memory module stores a program that is executable by the processing module, wherein the processing module by executing the program is configured to calculate a cadence frequency from the data received from the foot interaction sensor, to measure a first signal amplitude for the data detected at a first multiplier of the cadence frequency calculated, to measure a second signal amplitude for the data detected at a second multiplier at twice the cadence frequency calculated, and to compare the first signal amplitude and the second signal amplitude to determine a cadence factor;
    wherein the program also stores a predetermined threshold, wherein the processing module is configured to compare the cadence factor to the predetermined threshold, and wherein the processing module determines whether the user is walking or running based upon the comparison of the cadence factor to the predetermined threshold.

* * * * *